United States Patent
Arba Mosquera et al.

(10) Patent No.: US 11,890,232 B2
(45) Date of Patent: Feb. 6, 2024

(54) METHOD FOR CONTROLLING AN EYE SURGICAL LASER AND TREATMENT DEVICE

(71) Applicant: SCHWIND eye-tech-solutions GmbH, Kleinostheim (DE)

(72) Inventors: Samuel Arba Mosquera, Aschaffenburg (DE); Shwetabh Verma, Aschaffenburg (DE); Nico Triefenbach, Mainaschaff (DE); Mario Shraiki, Ober-Ramstadt (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 228 days.

(21) Appl. No.: 17/245,994

(22) Filed: Apr. 30, 2021

(65) Prior Publication Data
US 2021/0346198 A1 Nov. 11, 2021

(30) Foreign Application Priority Data

May 8, 2020 (DE) ...................... 10 2020 112 583.6

(51) Int. Cl.
*A61F 9/008* (2006.01)
*A61D 1/00* (2006.01)
(Continued)

(52) U.S. Cl.
CPC ........ *A61F 9/0084* (2013.01); *A61F 9/00827* (2013.01); *A61B 2017/0019* (2013.01);
(Continued)

(58) Field of Classification Search
CPC ................ A61F 9/0084; A61F 9/00827; A61F 2009/00872; A61F 2009/00882; A61F 2009/00897
See application file for complete search history.

(56) References Cited

U.S. PATENT DOCUMENTS

2004/0243111 A1 12/2004 Bendett et al.
2005/0107773 A1* 5/2005 Bergt ................. A61F 9/00836
606/4

(Continued)

FOREIGN PATENT DOCUMENTS

CA 2 620 095 A1 4/2007
DE 10 2005 049 281 A1 4/2007

OTHER PUBLICATIONS

Office Action dated Mar. 9, 2021 in corresponding German Patent Application No. 10 2020 112 583.6.

*Primary Examiner* — Nathan J Jenness
(74) *Attorney, Agent, or Firm* — MEDLER FERRO WOODHOUSE & MILLS PLLC

(57) ABSTRACT

Method for controlling an eye surgical laser of a treatment device for the separation of a volume body with a predefined posterior interface and a predefined anterior interface from a human or animal cornea. The method includes controlling the laser by means of a control device of the treatment device such that it emits pulsed laser pulses in a shot sequence in a predefined pattern into the cornea. The interfaces of the volume body are defined by the predefined pattern and are generated by means of an interaction of the individual laser pulses with the cornea by the generation of a plurality of cavitation bubbles by photodisruption along at least one cavitation bubble path. At least a partial area of an outer cavitation bubble path of the volume body is generated with a higher cavitation bubble density than an inner cavitation bubble path.

26 Claims, 3 Drawing Sheets

(51) Int. Cl.
*A61B 17/00* (2006.01)
*A61B 18/00* (2006.01)

(52) U.S. Cl.
CPC ...... *A61B 2018/00761* (2013.01); *A61D 1/00* (2013.01); *A61F 2009/00872* (2013.01); *A61F 2009/00882* (2013.01); *A61F 2009/00897* (2013.01)

(56) References Cited

U.S. PATENT DOCUMENTS

| | | | |
|---|---|---|---|
| 2005/0245915 A1* | 11/2005 | Loesel | A61F 9/00836 606/4 |
| 2007/0193987 A1* | 8/2007 | Bischoff | H01S 3/1308 219/121.73 |
| 2009/0137988 A1* | 5/2009 | Kurtz | A61F 9/00825 606/4 |
| 2010/0331830 A1* | 12/2010 | Bischoff | A61F 9/00838 606/5 |
| 2011/0206072 A1* | 8/2011 | Karavitis | H01S 3/10046 372/25 |
| 2012/0016351 A1 | 1/2012 | Stobrawa et al. | |
| 2017/0007395 A1 | 1/2017 | Peyman | |
| 2022/0347012 A1* | 11/2022 | Wirth | A61F 9/00804 |

* cited by examiner

METHOD FOR CONTROLLING AN EYE SURGICAL LASER AND TREATMENT DEVICE

The invention relates to a method for performing a surgical procedure on a human or animal cornea and to a method for controlling an eye surgical laser of a treatment device for the separation of a volume body with a predefined posterior interface and a predefined anterior interface from a human or animal cornea. Further, the invention relates to a treatment device, to a computer program as well as to a computer-readable medium.

Opacities and scars within the cornea, which can arise by inflammations, injuries or native diseases, impair the sight. In particular in case that these pathological and/or unnaturally altered areas of the cornea are located on the axis of vision of the eye, clear sight is considerably disturbed. Hereto, different laser methods by means of corresponding treatment devices are given from the prior art, which can separate a volume body from the cornea and thus can improve the sight for a patient. Applications of laser methods for refractive correction of a corneal curvature are also known. The laser method is in particular an invasive procedure such that it is of particular advantage for the patient if the procedure is performed in a time as short as possible and to a particularly efficient extent.

In small corrections on the cornea, a small and thin volume body, respectively, can preferably be removed from the cornea. However, herein, there is the danger that the volume body tears or breaks upon the separation from the cornea. A localization of a thin volume body upon the separation from the cornea can also be aggravated. Therefore, previous methods provide applying an additional plane-parallel layer to the volume body in order that an easier localization and separation can be performed. However, herein, it is disadvantageous that a larger corneal volume has to be removed.

It is the object of the present invention to provide a method for controlling an eye surgical laser, a method for performing a surgical procedure, a treatment device, a computer program as well as a computer-readable medium, by means of which an efficient, safe and fast treatment of an eye is ensured.

This object is solved by a method for controlling an eye surgical laser, a treatment device, a computer program as well as a computer-readable medium according to the independent claims. Advantageous configurations with convenient developments of the invention are specified in the respective dependent claims, wherein advantageous configurations of the method are to be regarded as advantageous configurations of the treatment device, of the computer program and of the computer-readable medium and vice versa.

An aspect of the invention relates to a method for performing a surgical procedure on a human or animal cornea for the separation of a volume body from the cornea and to a method for controlling an eye surgical laser of a treatment device for the separation of a volume body with a predefined posterior interface and a predefined anterior interface from a human or animal cornea. Controlling the laser by means of a control device of the treatment device such that it emits pulsed laser pulses in a shot sequence in a predefined pattern into the cornea is effected, wherein the interfaces of the volume body to be separated are defined by the predefined pattern and the interfaces are generated by means of an interaction of the individual laser pulses with the cornea by the generation of a plurality of cavitation bubbles generated by photodisruption, wherein the plurality of cavitation bubbles is generated along a cavitation bubble path having an outer cavitation bubble path section and an inner cavitation bubble path section, wherein at least a partial area of the outer cavitation bubble path of an outer edge area, as radially viewed, of the volume body to be separated is generated with a higher cavitation bubble density than the inner cavitation bubble path section.

Thereby, it is allowed that a higher cavitation bubble density is generated at least in a partial area of the outer edge area. Thereby, it is in particular allowed that a complete separation of the volume body from the cornea can be ensured in this area, whereby an improved and easier removal of the volume body is allowed. For example, the volume body to be separated can have a lower height in an anterior-posterior direction at the outer edge area, which is caused by a geometry of the volume body. With a non-complete separation from the cornea, therefore, the volume body could be damaged upon the removal, in particular in the edge area, whereby residues could remain, which would have to be expensively removed. By means of the higher cavitation bubble density at least in the partial area of the outer cavitation bubble path, a close photodisruption is generated, whereby an easier separation of the volume body from the cornea can be achieved and whereby an overall thinner volume body and thus a thicker cornea can also be achieved since the additional plane-parallel layer can be avoided.

In addition, the increased cavitation bubble density in the at least one partial area can serve as a marking, since an altered light refraction, that is scattered light ("scattering"), occurs at this location in the cornea due to the increased cavitation bubble density, which can be perceived from the outside. Thus, it is allowed to easier determine an edge of the volume body.

Accordingly, an efficient, safe and fast treatment of the eye can overall be allowed.

Preferably, the preset pattern can be rotationally symmetric or meander-shaped. For example, the preset pattern can be generated substantially circularly, in particular by means of concentric circles, or spirally. The outer edge area can be arranged circularly around the volume body, that is as a surface between two circular arcs with different radii, wherein the outer edge area can be located at the location of the volume body, at which the anterior and posterior interfaces converge, the so-called transition area. In particular, the outer edge area can comprise the outer ten percent of the volume body, as radially viewed, particularly preferably only the outer five percent of the volume body. In particular, as radially viewed from outside to inside, the outer edge area of the volume body can have a length of 500 micrometers, preferably less than 400 micrometers, particularly preferably 200 micrometers. Therein, the outer cavitation bubble path can extend within the outer edge area and the inner cavitation bubble path can extend in an area of the volume body, which extends from a central point of the volume body up to the outer edge area as radially viewed. Preferably, the outer edge area, in which the increased cavitation bubble density is generated, can belong to the anterior and/or the posterior interface.

It is meant by the at least one partial area that at least a part of the outer edge area is generated with the higher cavitation bubble density, for example a section or arc segment of the outer edge area. The higher cavitation bubble density means that a concentration of cavitation bubbles in a surface or a volume of the cornea is increased, wherein adjacent cavitation bubbles preferably overlap. For example, the higher cavitation bubble density can be generated in that adjacent cavitation bubbles overlap by at least 50% of their volume.

According to an advantageous form of configuration, the control of the laser is effected such that the higher cavitation bubble density is generated in an entire circumference of the outer edge area of the volume body to be separated. In other words, as radially viewed, the higher cavitation bubble density can cover an angle of 360 degrees within the outer edge area. For example, the higher cavitation bubble density can be generated for the entire circumference of the volume body in the transition area, in which the posterior and/or the anterior interface converge. Preferably, the cavitation bubble density can be generated at that interface, which is further outside as radially viewed. Particularly preferably, the anterior and the posterior interface can converge in an intersection curve, wherein the cavitation bubble path with the higher cavitation bubble density is generated circularly on the connecting line of the interfaces. Thereby, it is allowed that the entire volume body can be separated from the cornea in improved manner.

According to a further advantageous form of configuration, the control of the laser is effected such that the partial area, in which a higher cavitation bubble density is generated, is generated at the outer edge area of the volume body to be separated, which is arranged in the direction of an incision of the cornea. An incision is that area, in which the cornea is incised from the outside to remove the volume body. In particular, as radially viewed, the incision is arranged on an outer side of the transition area, thus outside of the volume body. In this form of configuration, the partial area, in which the higher cavitation bubble density is generated, is arranged in the direction of this incision. This has the advantage that the beginning of the volume body can be determined starting from the incision upon a removal of the volume body.

Furthermore, it is advantageous if the partial area, in which the higher cavitation bubble density is generated, is generated concentrically or parallel to the incision. This means that the partial area and the incision in the cornea are parallel to each other or, if the incision is circularly configured, concentric thereto. Thus, an improved recognition of the volume body can be achieved.

It is also advantageous if the partial area is generated with a length greater than or equal to a length of the incision. In other words, the length of the partial area is at least as long as the length of the incision. Hereby, a better recognition of the volume body and thus a more reliable separation of the volume body can be allowed.

According to an advantageous form of configuration, the control of the laser is effected such that at least the one partial area is generated in an anterior-posterior direction over an entire height of the volume body to be separated, which the volume body has in the edge area. In other words, the volume body is completely separated from the cornea in its height by the increased cavitation bubble density in the edge area. In particular, the height of the volume body in the edge area can be a distance in the anterior-posterior direction, which is present between the two interfaces. Herein, the anterior-posterior direction is the direction, which extends parallel to the optical axis of the eye. By this form of configuration, an improved separation of the volume body from the cornea is allowed.

According to an advantageous form of configuration, the higher cavitation bubble density is generated depending on a repetition frequency of the laser and/or a distance of the respective cavitation bubbles to each other. In other words, the repetition frequency of the laser, with which laser pulses are radiated into the cornea for generating the volume body, can be increased with a consistent movement speed of the laser to generate the higher cavitation bubble density, and/or the distances of the respective cavitation bubbles to each other can be reduced, for example by reducing the movement speed of the laser. Particularly preferably, both the movement speed of the laser can be reduced and the repetition frequency of the laser can be increased.

It is further advantageous if the repetition frequency of the laser is radially outwards increased depending on a position of the cavitation bubble in the cornea and/or the distance of the respective cavitation bubbles is radially outwards reduced depending on a position of the cavitation bubble in the cornea. In other words, as radially viewed, the cavitation bubble density increases on and on from inside to outside such that the highest cavitation bubble density is present in the outer edge area. That is, the cavitation bubble density increases depending on the radius or the distance from the center of the volume body. This is advantageous since a height or thickness of the volume body can decrease from inside towards the outside. This means that breaking of the volume body towards the outside is more likely by the low height. By this form of configuration, it is allowed that a separation of the volume body from the cornea, in particular in the areas with low height, can be improved.

According to an advantageous form of configuration, the control of the laser is effected such that the higher cavitation bubble density is generated by tracing at least the partial area of the outer cavitation bubble path multiple times. In other words, in the edge area, the outer cavitation bubble path is repeated multiple times one after the other at least in the partial area, such that this outer cavitation bubble path has the highest cavitation bubble density. Thus, an improved separation at least of the partial area from the cornea can be generated.

According to a further advantageous form of configuration, the control of the laser is effected such that, for generating the volume body, the posterior interface is generated from inside to outside and the anterior interface is generated from outside to inside, as radially viewed, by the predefined pattern, or wherein the anterior interface is generated from inside to outside and the posterior interface is generated from outside to inside, wherein the outer cavitation bubble path of the outer edge area of the volume body is respectively generated as an intersection curve of the interfaces. In other words, the interfaces are generated in that it is started at one interface on the inside as radially viewed and the interface is generated towards the outside by the predefined pattern. At the outermost position of the first interface, the laser can reverse and seamlessly begin with the separation of the other interface from outside to inside, respectively. This means that the entire volume body can be generated in one piece without stopping. In particular, the outer cavitation bubble path can represent the end of the first interface and the beginning of the second interface at the same time. Herein, the outer cavitation bubble path can preferably be traced by the laser at least twice, at the end and start of the respective interface. Hereby, the advantage arises that the interfaces are contiguous and thus an improved separation of the volume body from the cornea can be achieved.

Furthermore, it is advantageous if the control of the laser is effected such that a lenticular volume body is separated. In other words, the volume body can therein be lenticularly formed, whereby a simple removal via a cut or via an opening in the cornea, that is the incision, is possible. In that the volume body to be separated is only described and defined by the interfaces and the interfaces for example encompass the pathological and/or unnaturally altered tissue or the corresponding altered area on the one hand and are generated by means of photodisruption on the other hand, a full-surface or full-volume ablation of the volume body can be omitted. Only the interfaces are generated by means of photodisruption such that the predefined volume body can subsequently be withdrawn from the cornea.

It is further advantageous if the control of the laser is effected such that topographic and/or pachymetric and/or morphologic data of the cornea is taken into account. Thus, topographic and/or pachymetric measurements of the cornea to be treated as well as the type, the position and the extent of the for example pathological and/or unnaturally altered area within the stroma of the cornea in particular can be taken into account. In particular, control datasets are generated at least by providing topographic and/or pachymetric and/or morphologic data of the untreated cornea and providing topographic and/or pachymetric and/or morphologic data of the pathological and/or unnaturally altered area to be removed within the cornea.

According to a further advantageous form of configuration, the control of the laser is effected such that the laser emits laser pulses in a wavelength range between 300 nanometers and 1,400 nanometers, in particular between 700 nanometers and 1,200 nanometers, at a respective pulse duration between 1 fs and 1 ns, in particular between 10 fs and 10 ps, and a repetition frequency of greater than 10 kHz, in particular between 100 kHz and 100 MHz. Such lasers are already used for photodisruptive methods in the eye surgery. The produced lenticule is subsequently removed via the incision in the cornea. However, the use of such photodisruptive lasers instead of ablatively acting lasers is new and not known from the prior art. The use of photodisruptive lasers in the method according to the invention additionally has the advantage that the irradiation of the cornea is not to be effected in a wavelength range below 300 nm. This range is subsumed by the term "deep ultraviolet" in the laser technology. Thereby, it is advantageously avoided that an unintended damage to the cornea is effected by this very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy in the generation of the interfaces is ensured.

A further aspect of the invention relates to a treatment device with at least one eye surgical laser for the separation of a volume body with predefined interfaces of a human or animal eye by means of photodisruption and with at least one control device for the laser or lasers, which is formed to execute the steps of the method according to the preceding aspect. The treatment device according to the invention allows that disadvantages occurring in the use of usual ablative treatment devices, namely relatively long treatment times and relatively high energy input by the laser into the cornea, are reliably avoided. These advantages are in particular achieved by the formation of the eye surgical laser as a photodisruptive laser.

Therein, the laser is suitable to emit laser pulses in a wavelength range between 300 nm and 1,400 nm, preferably between 700 nm and 1,200 nm, at a respective pulse duration between 1 fs and 1 ns, preferably between 10 fs and 10 ps, and a repetition frequency of greater than 10 kHz, preferably between 100 kHz and 100 MHz.

In an advantageous form of configuration of the treatment device, the treatment device comprises a storage device for at least temporary storage of at least one control dataset, wherein the control dataset or datasets include(s) control data for positioning and/or focusing individual laser pulses in the cornea, and includes at least one beam device for beam guidance and/or beam shaping and/or beam deflection and/or beam focusing of a laser beam of the laser. In particular, the treatment device is formed as a rotational scanner. Therein, the mentioned control datasets are usually generated based on a measured topography and/or pachymetry and/or morphology of the cornea to be treated and the type of the pathologically and/or unnaturally altered area to be removed within the cornea.

Further features and the advantages thereof can be taken from the descriptions of the first inventive aspect, wherein advantageous configurations of each inventive aspect are to be regarded as advantageous configurations of the respectively other inventive aspect.

A third aspect of the invention relates to a computer program including instructions, which cause the treatment device according to the second inventive aspect to execute the method steps according to the first inventive aspect.

A fourth aspect of the invention relates to a computer-readable medium, on which the computer program according to the third inventive aspect is stored. Further features and the advantages thereof can be taken from the descriptions of the first and second inventive aspects, wherein advantageous configurations of each inventive aspect are to be regarded as advantageous configurations of the respectively other inventive aspect.

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

In the figures, identical or functionally identical elements are provided with the same reference characters.

Figure 1:
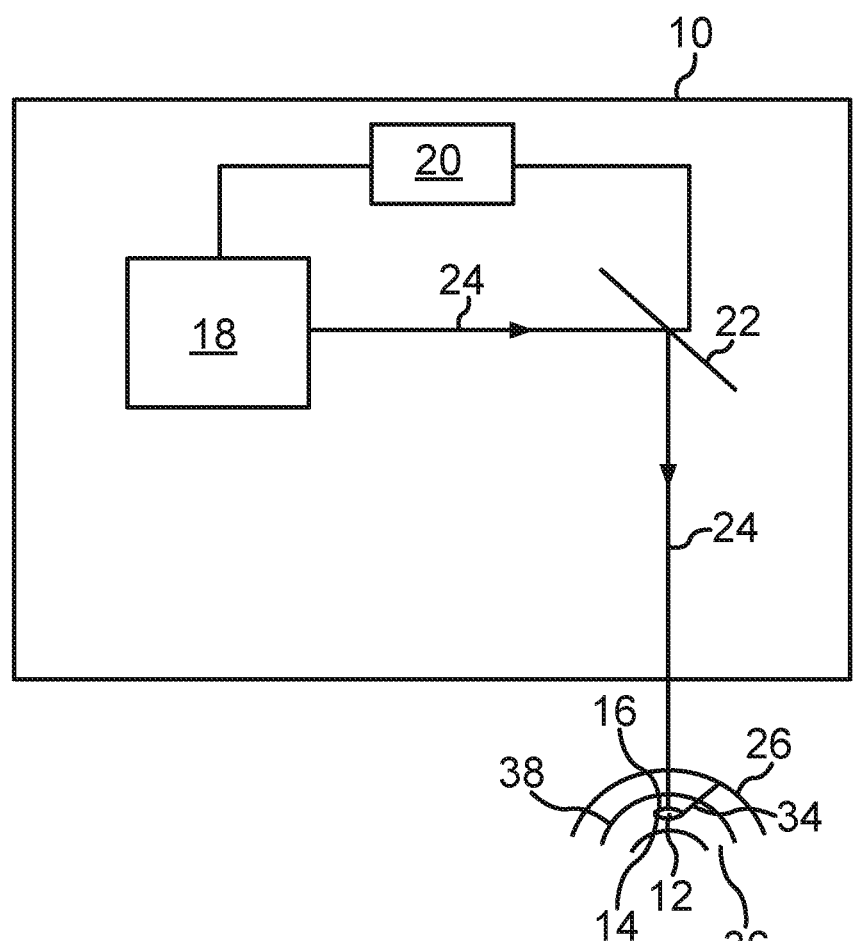
FIG. 1 is a schematic side view of an embodiment of a treatment device.

FIG. 1 shows a schematic representation of a treatment device 10 with an eye surgical laser 18 for the separation of a predefined corneal volume or volume body 12 with predefined interfaces 14, 16 of a cornea of a human or animal eye by means of photodisruption. One recognizes that a control device 20 for the laser 18 is formed besides the laser 18, such that it emits pulsed laser pulses in a predefined pattern into the cornea, wherein the interfaces 14, 16 of the volume body 12 to be separated are generated by the predefined pattern by means of photodisruption. In the illustrated embodiment, the interfaces 14, 16 form a lenticular volume body 12, wherein the position of the volume body 12 is selected in this embodiment such that a pathological and/or unnaturally altered area within a stroma 36 of the cornea is enclosed. Furthermore, it is apparent from FIG. 1 that the so-called Bowman's membrane 38 is formed between the stroma 36 and an epithelium.

Furthermore, one recognizes that the laser beam 24 generated by the laser 18 is deflected towards a surface 26 of the cornea by means of a beam device 22, namely a beam deflection device such as for example a rotational scanner. The beam deflection device is also controlled by the control device 20 to generate the mentioned predefined pattern in the cornea.

The illustrated laser 18 is a photodisruptive laser, which is formed to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 KHz, preferably between 100 kHz and 100 MHz.

In addition, the control device 20 comprises a storage device (not illustrated) for at least temporary storage of at least one control dataset, wherein the control dataset or datasets include(s) control data for positioning and/or for focusing individual laser pulses in the cornea. The position data and/or focusing data of the individual laser pulses are generated based on a previously measured topography and/or pachymetry and/or the morphology of the cornea and the pathological and/or unnaturally altered area for example to be removed within the stroma 36 of the eye.

Figure 2:
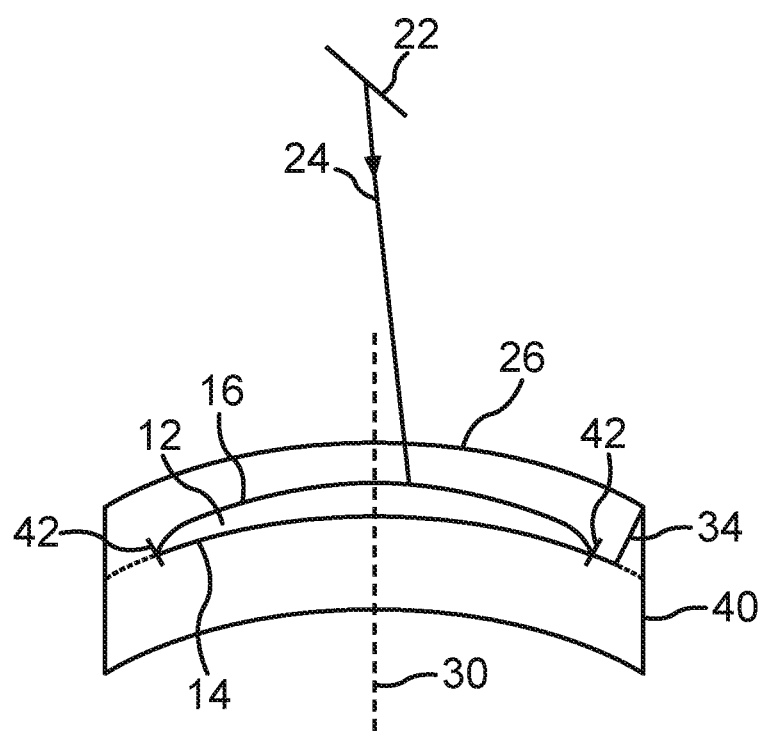
FIG. 2 is a schematic side view of an embodiment of a treatment device.

FIG. 2 shows a schematic diagram of the generation of the volume body 12 to be separated according to an embodiment of the present method. One recognizes that the interfaces 14, 16 are generated by means of the pulsed laser beam 24, which is directed towards the cornea 40 or towards the surface 26 of the cornea via the beam device 22. Therein, the anterior interface 16 and the posterior interface 14 form a lenticular volume body 12, which is to be separated for correcting the cornea 40. Furthermore, an incision 34 in the cornea 40 is illustrated in this embodiment, which is generated by a cut from the surface 26 of the cornea with a predefined angle and with a predefined geometry to the volume body 12, wherein the cut can also be generated by means of the laser 18. The volume body 12 defined by the interfaces 14, 16 can then be removed from the cornea 40 via the incision 34.

In the illustrated embodiment, the interface 14, that is the interface located deeper in the eye in the direction of an optical axis 30, is first formed by means of the laser beam 24, wherein it then corresponds to the posterior interface 14. This can be effected by at least partially circularly and/or spirally guiding the laser beam 24 according to the predefined pattern. Subsequently, the interface 16 is generated in comparable manner, which then corresponds to the anterior interface 16, such that the interfaces 14, 16 form the lenticular volume body 12. Also, the incision 34 can for example also be generated by the laser 18. However, the order of the generation of the interfaces 14, 16 and the incision 34 can also be changed.

Preferably, it is provided that before, during or after the generation of the interfaces 14, 16, at least a partial area 42 of an outer cavitation bubble path section of an outer edge area 50 (FIG. 3), as radially viewed, of the volume body 12 to be separated is generated with a higher cavitation bubble density than an inner cavitation bubble path section. This means that the partial area 42 is generated starting from the optical axis 30 to the outer edge area 50 of the volume body 12 in that the repetition frequency of the laser and/or a distance of the respective cavitation bubbles to each other in the outer cavitation bubble path section is higher than an interior cavitation bubble path section. In this embodiment, the partial area 42 can be generated over an entire circumference of the outer edge area 50 of the volume body 12 to be separated, wherein the partial area 42 is here illustrated as a straight line in simplified manner. Preferably, the partial area 42 can be an area with increased cavitation bubble density in the outer edge area of the posterior interface 14 and/or the anterior interface 16. That area is meant by outer edge area 50 (FIG. 3), at which the interfaces converge, that is the transition area of the interfaces 14, 16, in particular, the outer area, as radially viewed, that is from the optical axis 30 towards the edges of the volume body 12, can include the outer ten percent. The outer cavitation bubble path section with the higher cavitation bubble density can then be generated in this outer edge area 50, wherein the partial area 42 is preferably generated over an entire height of the volume body 12 to be separated, which the volume body 12 has in the edge area 50. Herein, the height of the volume body 12 to be separated is meant in an anterior-posterior direction, that is parallel to the optical axis 30.

For generating the higher cavitation bubble density in the partial area 42, the outer cavitation bubble path section can for example be generated by tracing at least the partial area 42 multiple times, for example in that the laser 24 traces the outer cavitation bubble path section two to ten times in the partial area 42. Particularly preferably, it can be provided that the control of the laser 18 is effected such that the posterior interface 14 is first generated spirally outwards from the center by means of the predefined pattern, wherein the cavitation bubble density can increase from inside to outside, that is radially outwards, depending on a position of the cavitation bubble in the cornea 40 until the highest cavitation bubble density is generated in the partial area 42. Subsequently, the generation of the anterior interface 16 can be begun without interrupting the predefined pattern, such that an intersection curve of the interfaces 14, 16 forms in the partial area 42, wherein the cavitation bubble density herein can decrease from outside to inside as radially viewed depending on the position of the cavitation bubble. Thus, the volume body 12 can be generated in one piece, wherein the cavitation bubble density increases from inside to outside until it reaches its maximum in the outer cavitation bubble path section in the partial area 42. Hereby, a complete separation from the cornea 40 can be achieved, in particular in the areas of the volume body 12, which has a low height, whereby the volume body can be more easily extracted via the incision 34.

Figure 3:
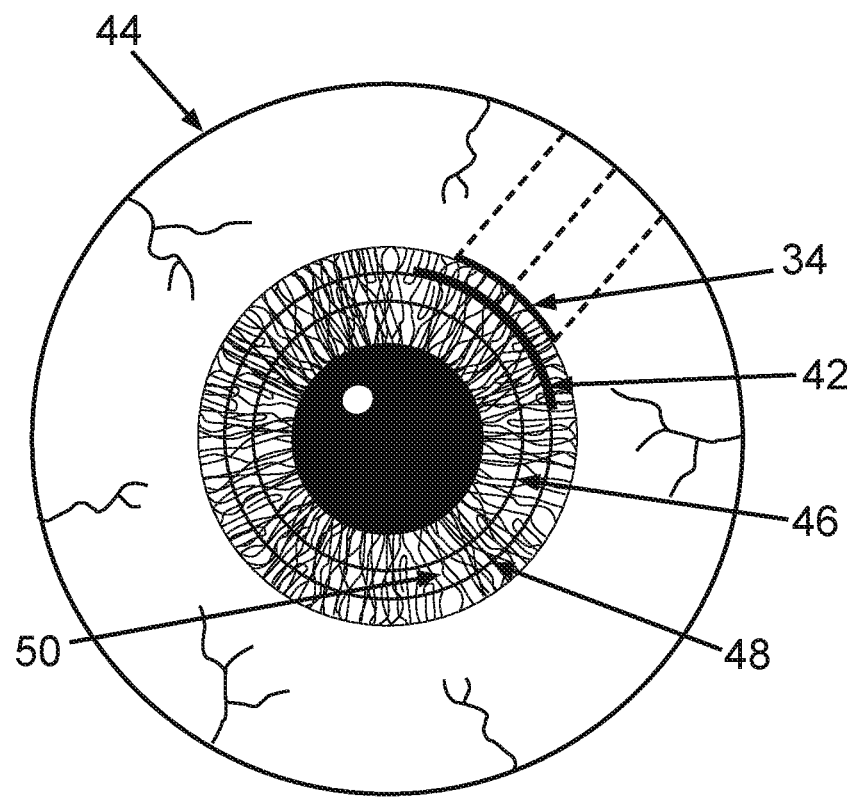
FIG. 3 is a schematic top view to an eye from the direction of a treatment device.

FIG. 3 shows a schematic diagram for generating the volume body 12 to be separated according to an embodiment of the present method. In this embodiment, a view from the direction of the treatment device 10 in an anterior-posterior direction, that is along the optical axis 30, to the cornea 40 of an eye 44 is illustrated. From a center of the eye 44 up to an edge 46, as radially viewed, there is the so-called optical zone, in which a complete correction of the refractive power of the eye 44 is to occur. From the edge 46 further outwards, there is the lenticule edge 48, at which the interfaces 14, 16 encounter each other, wherein the lenticule edge 48 can represent the end of the transition area. Between the edge 46 of the optical zone and the lenticule edge 48, there is the outer edge area 50, in which the outer cavitation bubble path section with the increased cavitation bubble density is provided, wherein the outer edge area 50 encompasses the edge 46 of the optical zone and the lenticule edge 48. Preferably, a distance of 500 micrometers or less is preferably provided between the edge 46 of the optical zone and the lenticule edge 48. In this embodiment, the outer cavitation bubble path section, which comprises the partial area 42 with the higher cavitation bubble density, can be located at or on the lenticule edge 48.

From the lenticule edge 48 further radially outwards, the incision 34 can be provided, through which the volume body 12 can be removed from the cornea. In this embodiment, the partial area 42 cannot extend over the entire circumference of the outer edge area 50, in particular the outer cavitation bubble path section of the lenticule edge 48, but only in the partial area 42, which is arranged in the direction of the incision 34. Herein, the partial area 42 with the higher cavitation bubble density is preferably arranged concentrically to the incision 34 and has a length, which is equal to or longer than the length of the incision 34. The higher volume density in the partial area 42 can for example be generated by repeating the circular arc in the partial area 42 multiple times, for example in that the sector with the same diameter and the same depth is repeated ten to thirty times. Hereby, a different light refraction characteristic results, whereby an edge of the volume body 12 can be more easily determined. Thus, coming from the direction of the incision 34, it can be determined where the volume body 12 begins. Particularly preferably, the entire outer cavitation bubble path section of the lenticule edge 48 can be generated with the increased cavitation bubble density, wherein the cavitation bubble density is additionally increased in the partial area 42. For example in that tracing multiple times occurs in the partial area 42 illustrated here. For example, the outer cavitation bubble path section can be traced ten times by the laser beam and the partial area 42 can be traced twenty times in addition thereto. Thus, it can be achieved that the volume body 12 can be easily detached from the cornea 40 on the one hand and a marking is present in the direction of the incision 34 on the other hand, at which the beginning of the volume body is additionally more easily recognizable.

Overall, thinner volume bodies 12 can be formed with the treatment device and the method since a better detachment of the volume body from the cornea through the incision can be achieved, since a danger is reduced that the volume body formed as a lenticule breaks upon removal.

What is claimed is:

1. A method for controlling an eye surgical laser of a treatment device for separation of a volume body with a predefined posterior interface and a predefined anterior interface from a human or animal cornea, comprising:
    controlling the laser by means of a control device of the treatment device such that the laser emits pulsed laser pulses in a shot sequence in a predefined pattern into the cornea,
    wherein the posterior and anterior interfaces of the volume body to be separated are defined by the predefined pattern, and the posterior and anterior interfaces are generated by means of an interaction between each of the laser pulses with the cornea due to a plurality of cavitation bubbles being generated by photodisruption,
    wherein the plurality of cavitation bubbles is generated along a cavitation bubble path having an outer cavitation bubble path section and an inner cavitation bubble path section, and
    wherein at least a partial area of the outer cavitation bubble path section of an outer edge area, as radially viewed, of the volume body to be separated is generated with a higher cavitation bubble density than the inner cavitation bubble path section.

2. The method according to claim 1, wherein controlling the laser is affected such that the higher cavitation bubble density is generated over an entire circumference of the outer edge area of the volume body to be separated.

3. The method according to claim 1, wherein controlling the laser is affected such that the partial area, in which the higher cavitation bubble density is generated, is generated at the outer edge area of the volume body to be separated, which is arranged in a direction of an incision of the cornea.

4. The method according to claim 3, wherein the partial area is generated concentrically or parallel to the incision.

5. The method according to claim 3, wherein the partial area is generated with a length greater than or equal to a length of the incision.

6. The method according to claim 1, wherein controlling the laser is affected such that the partial area is generated in an anterior-posterior direction over an entire height, in the outer edge area, of the volume body to be separated.

7. The method according to claim 1, wherein the higher cavitation bubble density is generated depending on a repetition frequency of the laser and/or a distance between respective cavitation bubbles.

8. The method according to claim 7, wherein the repetition frequency of the laser is increased radially outwards depending on a position of the cavitation bubble in the cornea and/or the distance between the respective cavitation bubbles is reduced radially outwards depending on a position of the cavitation bubble in the cornea.

9. The method according to claim 1, wherein controlling the laser is affected such that the higher cavitation bubble density is generated by tracing at least the partial area of the outer cavitation bubble path section multiple times.

10. The method according to claim 1, wherein controlling the laser is effected such that for generating the volume body, the posterior interface is generated from inside to outside and the anterior interface is generated from outside to inside, as radially viewed, by the predefined pattern, or wherein the anterior interface is generated from inside to outside and the posterior interface is generated from outside to inside, wherein the outer cavitation bubble path section of the outer edge area of the volume body is respectively generated as an intersection curve of the posterior and anterior interfaces.

11. The method according to claim 1, wherein controlling the laser is affected such that a lenticular volume body is separated.

12. The method according to claim 1, wherein controlling the laser is affected such that topographic and/or pachymetric and/or morphologic data of the cornea is taken into account.

13. The method according to claim 1, wherein controlling the laser is affected such that the laser emits laser pulses in a wavelength range between 300 nm and 1400 nm, or between 700 nm and 1200 nm, at a respective pulse duration between 1 fs and 1 ns, or between 10 fs and 10 ps, and a repetition frequency of greater than 10 kHz, or between 100 kHz and 100 MHz.

14. A treatment device with at least one eye surgical laser for separation of a volume body with predefined posterior and anterior interfaces of a human or animal eye by means of photodisruption and with at least one control device for controlling the at least one eye surgical laser to perform the method according to claim 1.

15. The treatment device according to claim 14, wherein the control device comprises:
- at least one storage device for at least temporary storage of at least one control dataset, wherein the control dataset or datasets include(s) control data for positioning and/or focusing individual laser pulses in the cornea; and
- at least one beam device for beam guidance and/or beam shaping and/or beam deflection and/or beam focusing of a laser beam of the laser.

16. A non-transitory computer-readable medium, on which a computer program is stored, the computer program including instructions that cause at least one control device to control at least one eye surgical laser of a treatment device to execute the method steps according to claim 1, wherein the treatment device includes
- the at least one eye surgical laser for separation of a volume body with predefined posterior and anterior interfaces of a human or animal eye by means of photodisruption, and
- the at least one control device for controlling the at least one eye surgical laser during performance of the method.

17. A method for performing a surgical procedure on a human or animal cornea for separation of a volume body from the cornea, wherein for separating the volume body by an eye surgical laser, a plurality of cavitation bubbles is generated along a cavitation bubble path in the cornea, the cavitation bubble path having an outer cavitation bubble path section and an inner cavitation bubble path section, and wherein at least a partial area of the outer cavitation bubble path section of an outer edge area, as radially viewed, of the volume body to be separated is generated with a higher cavitation bubble density than the inner cavitation bubble path section.

18. The method for performing a surgical procedure according to claim 17, wherein the higher cavitation bubble density is generated over an entire circumference of the outer edge area of the volume body to be separated.

19. The method for performing a surgical procedure according to claim 17, wherein the partial area, in which the higher cavitation bubble density is generated, is generated at the outer edge area of the volume body to be separated, which is arranged in a direction of an incision of the cornea.

20. The method for performing a surgical procedure according to claim 19, wherein the partial area is generated concentrically or parallel to the incision.

21. The method for performing a surgical procedure according to claim 19, wherein the partial area is generated with a length greater than or equal to a length of the incision.

22. The method for performing a surgical procedure according to claim 17, wherein the partial area is generated in an anterior-posterior direction over an entire height, in the outer edge area, of the volume body to be separated.

23. The method for performing a surgical procedure according to claim 17, wherein the higher cavitation bubble density is generated depending on a repetition frequency of the laser and/or a distance between respective cavitation bubbles.

24. The method for performing a surgical procedure according to claim 23, wherein the repetition frequency of the laser is radially outwards increased depending on a position of the cavitation bubble in the cornea and/or the distance between the respective cavitation bubbles is radially outwards reduced depending on a position of the cavitation bubble in the cornea.

25. The method for performing a surgical procedure according to claim 17, wherein the higher cavitation bubble density is generated by tracing at least the partial area of the outer cavitation bubble path section multiple times.

26. The method for performing a surgical procedure according to claim 17, wherein for generating the volume body, a posterior interface of the volume body is generated from inside to outside and an anterior interface of the volume body is generated from outside to inside, as radially viewed, or wherein the anterior interface is generated from inside to outside and the posterior interface is generated from outside to inside, wherein the outer cavitation bubble path section of the outer edge area of the volume body is respectively generated as an intersection curve of the posterior and anterior interfaces.

* * * * *